US006309386B1

(12) United States Patent
Bek (10) Patent No.: US 6,309,386 B1
(45) Date of Patent: *Oct. 30, 2001

(54) LINEAR POWER CONTROL WITH PSK REGULATION

(75) Inventor: Robin B. Bek, Campbell, CA (US)

(73) Assignee: Somnus Medical Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/167,412

(22) Filed: Oct. 6, 1998

Related U.S. Application Data

(60) Provisional application No. 60/061,193, filed on Oct. 6, 1997, provisional application No. 60/062,458, filed on Oct. 6, 1997, provisional application No. 60/061,197, filed on Oct. 6, 1997, provisional application No. 60/061,714, filed on Oct. 6, 1997, provisional application No. 60/062,543, filed on Oct. 6, 1997, and provisional application No. 60/061,213, filed on Oct. 6, 1997.

(51) Int. Cl.[7] ................................................. A61B 18/04
(52) U.S. Cl. .............................. 606/34; 606/46; 606/48; 607/101
(58) Field of Search ................................ 606/32, 34, 35, 606/36, 38, 40, 41, 42, 45, 46, 48, 50; 607/97, 101, 122

(56) References Cited

U.S. PATENT DOCUMENTS 1,798,902    3/1931    Raney .
3,901,241    8/1975    Allen, Jr. .......................... 128/303.1

(List continued on next page.)

FOREIGN PATENT DOCUMENTS 43 03 882    2/1995    (DE) .
38 38 840    2/1997    (DE) .

(List continued on next page.)

OTHER PUBLICATIONS

Kaneko, et al., *Physiological Laryngeal Pacemaker*, May 1985, Trans Am Soc Artif Intern Organs , vol. XXXI, pp. 293–296.

(List continued on next page.)

*Primary Examiner*—Linda C. M. Dvorak
*Assistant Examiner*—David M. Ruddy
(74) *Attorney, Agent, or Firm*—Wilson Sonsini Goodrich & Rosati

(57) ABSTRACT

It is an object of the present invention to provide a multi-channel radio frequency (RF) power delivery and control system for applying energy to multiple electrodes of an RF tissue heating device.

In a first embodiment of the invention an apparatus for controlling electrical cross-talk in an electro-surgical instrument is disclosed. The apparatus includes: a driver, a first electrode, a second electrode, a ground for delivery of power to a surgical site, a power measurement circuit and a waveform generator. The power measurement circuit computes differences between a target power and an actual power delivered to the first electrode and the second electrode to establish an amount by which to increase and to decrease the power emanating from the first electrode and the second electrode. The waveform generator modulates a driver signal generated by the driver to increase and to decrease an integer number of whole wavelengths of the driver signal to produce a first oscillating signal measured at the first electrode and a second oscillating signal measured at the second electrode.

In an alternate embodiment of the invention a method for power control in an electro-surgical instrument is disclosed.

16 Claims, 8 Drawing Sheets

U.S. PATENT DOCUMENTS

| | | | |
|---|---|---|---|
| 4,011,872 | 3/1977 | Komiya | 128/303.14 |
| 4,196,724 | 4/1980 | Wirt et al. | 128/136 |
| 4,411,266 | 10/1983 | Cosman | 128/303.18 |
| 4,423,812 | 1/1984 | Sato | 206/387 |
| 4,532,924 | 8/1985 | Auth et al. | 128/303.17 |
| 4,565,200 | 1/1986 | Cosman | 128/642 |
| 4,727,874 * | 3/1988 | Bowers et al. | 606/38 |
| 4,901,737 | 2/1990 | Toone | 128/848 |
| 4,906,203 | 3/1990 | Margrave et al. | 439/188 |
| 4,907,589 | 3/1990 | Cosman | 606/34 |
| 4,943,290 | 7/1990 | Rexroth et al. | 606/45 |
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,233,515 | 8/1993 | Cosman | 364/413.02 |
| 5,256,138 | 10/1993 | Burek et al. | 606/42 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,216 | 1/1994 | Klicek | 606/42 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,316,020 | 5/1994 | Truffer | 128/848 |
| 5,328,467 | 7/1994 | Edwards et al. | 604/95 |
| 5,334,196 | 8/1994 | Scott et al. | 606/138 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,365,945 | 11/1994 | Halstrom | 128/848 |
| 5,366,490 | 11/1994 | Edwards et al. | 607/99 |
| 5,368,557 | 11/1994 | Nita et al. | 604/22 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,401,272 | 3/1995 | Perkins | 606/15 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,423,812 | 6/1995 | Ellman et al. | 606/45 |
| 5,433,739 | 7/1995 | Sluijter et al. | 607/99 |
| 5,435,805 | 7/1995 | Edwards et al. | 604/22 |
| 5,441,499 | 8/1995 | Fritzsch | 606/45 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 * | 1/1996 | Edwards et al. | 604/22 |
| 5,486,161 | 1/1996 | Lax et al. | 604/22 |
| 5,505,728 | 4/1996 | Ellman et al. | 606/39 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 * | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,545,434 | 8/1996 | Huarng | 427/243 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |
| 5,599,345 | 2/1997 | Edwards et al. | 606/41 |
| 5,609,151 | 3/1997 | Mulier et al. | 128/642 |
| 5,624,439 | 4/1997 | Edwards et al. | 606/45 |
| 5,817,093 * | 10/1998 | IV et al. | 606/50 |
| 5,931,836 * | 8/1999 | Hatta et al. | 606/38 |

FOREIGN PATENT DOCUMENTS

| | | |
|---|---|---|
| 0 139 607 A1 | 5/1985 | (EP). |
| 0 608 609 A2 | 8/1994 | (EP). |
| 92/10142 | 6/1992 | (WO). |
| 93/08755 | 5/1993 | (WO). |
| 94/10925 | 5/1994 | (WO). |
| 94/26178 | 11/1994 | (WO). |
| 95/18575 | 7/1995 | (WO). |
| 95/19142 | 7/1995 | (WO). |
| 95/25472 | 9/1995 | (WO). |
| WO 97/20510 | 6/1997 | (WO) .......... A61B/17/39 |

OTHER PUBLICATIONS

Mugica, et al., *Direct Diaphragm Stimulation*, Jan., 1987, PACE, vol. 10, pp. 252–256.

Mugica, et al., *Neurostimulation: An Overview*, Chapter 21, *Preliminary Test of a Muscular Diaphragm Pacing System on Human Patients*, 1985, pp. 263–279.

Nochomovitz, et al., *Electrical Activation of the Diaphragm*, Jun. 1988, Clinics in Chest Medicine, vol. 9, No. 2,, pp.349–358.

Prior, et al., *Treatment of Menorrhagia by Radiofrequency Heating*, 1991, Int. J. Hyperthermia, vol. 7, pp, 213–220.

Rice, et al., *Endoscopic Paranasal Sinus Surgery*, Chapter 5, *Functional Endoscopic Paranasal Sinus Surgery, The Technique of Messerklinger*, Raven Press, 1988, pp.75–104.

Rice et al., *Endoscopic Paranasal Sinus Surgery*, Chapter 6, *Total Endoscopic Sphenoethmoidectomy*, The Technique of Wigand, Raven Press, 1988, pp.105–125.

* cited by examiner

MONOPOLAR OPERATION

BIPOLAR OPERATION

COMBINED MONOPOLAR AND BIPOLAR OPERATION

LINEAR POWER CONTROL WITH PSK REGULATION

CROSS REFERENCE TO RELATED APPLICATION

This application claims the benefit of prior filed copending Provisional Application No. 60/061,193, filed on Oct. 6, 1997, entitled Linear Power Control With PSK Regulation, Provisional Application No. 60/062,458, filed on Oct. 6, 1997, entitled Linear Power Control With Digital Phase Lock, Provisional Application, Provisional Application No. 60/061,197, filed on Oct. 6, 1997, entitled Memory for Regulating Device Utilization and Behavior, Provisional Application No. 60/061,714, filed on Oct. 6, 1997, entitled Dual Processor Architecture For Electro Generator, Provisional Application No. 60/062,543, filed on Oct. 6, 1997, entitled Method And Apparatus For Power Measurement In Radio Frequency Electro-Surgical Generators, and Provisional Application No. 60/061,213, filed on Oct. 6, 1997, entitled Method And Apparatus for Impedance Measurement In A Multi-Channel Electro-Surgical Generator.

The present application is related to copending U.S. patent application Ser. No. 09/167,217, filed Oct. 6, 1998, entitled Linear Power Control With Digital Phase Lock, U.S. patent application Ser. No. 09/167,222, filed Oct. 6, 1998, entitled Memory for Regulating Device Utilization and Behavior, U.S. patent application Ser. No. 09/167,508, filed Oct. 6, 1998, entitled Dual Processor Architecture For Electro Generator, U.S. patent application Ser. No. 09/167,505, filed Oct. 6, 1998, entitled Method And Apparatus For Power Measurement In Radio Frequency Electro-Surgical Generators, U.S. patent application Ser. No. 09/167,215, filed Oct. 6, 1998, entitled Method And Apparatus for Impedance Measurement In A Multi-Channel Electro-Surgical Generator, International Application No. PCT/U.S. 98/21065, filed Oct. 6, 1998, entitled Linear Power Control With Digital Phase Lock, and International Application No. PCT/4598/21065, filed October 1998, entitled Dual Processor Architecture For Electro Generator.

Each of the above-cited applications is incorporated herein by reference in its entirety.

BACKGROUND OF THE INVENTION

1. Field of the Invention

This invention relates to the field of electro-surgical medical devices. More particularly, this invention relates to devices that deliver energy in the form of radio-frequency electrical current to tissue in order to perform surgical functions.

2. Description of Related Art

Various medical procedures rely on high-frequency electrical currents to deposit energy and thus heat human and animal tissues. During such procedures, a high-frequency current is passed through the tissue between electrodes. One electrode is located at the tip of a surgical probe. Another electrode is located elsewhere, and may be a ground pad or another surgical probe tip. The tissue to be treated lies between the electrodes.

When the electrode circuit is energized, the electric potential of the electrodes at the probe tips oscillates at radio frequencies about a reference potential. If one is used, a ground pad remains at a floating reference potential. As the electric potential of the probe electrodes varies, a motive force on charged particles in the tissue is established that is proportional to the gradient of the electric potential. This electromotive force causes a net flow of electric charge, a current, to flow from one electrode, through the tissue, to any other electrode(s) at a lower potential. In the course of their flow, the charged particles collide with tissue molecules and atoms. This process acts to convert electrical energy to sensible heat in the tissue and is termed Joule heating.

Upon heating, surgical functions such as cutting, cauterizing and tissue destruction can be accomplished. For example, tissues can be cut by heating and eventually vaporizing the tissue cell fluids. The vaporization causes the cell walls to rupture and the tissue to cleave. When it is beneficial to destroy tissue, comparatively higher rates of energy deposition can cause tissue ablation.

Ablation of cellular tissues in situ is used in the treatment of many diseases and medical conditions either alone or combined with surgical removal procedures. Surgical ablation is often less traumatic than surgical removal procedures and may be the only alternative where other procedures are unsafe.

Tissue ablation devices commonly utilize electromagnetic (microwave, radio frequency (RF), lasers) or mechanical (acoustic) energy. In the category of electro-surgical devices, microwave ablation systems utilize a microwave antenna which is inserted into a natural body opening through a duct to the zone of treatment. Electromagnetic energy then radiates from the antenna through the duct wall into the target tissue. However, there is often severe trauma to the duct wall in this procedure since there is a significant microwave energy flux in the vicinity of the intended target. The energy deposition is not sufficiently localized. To reduce this trauma, many microwave ablation devices use a cooling system. However, such a cooling system complicates the device and makes it bulky. Laser ablation devices also suffer the same drawback as microwave systems. The energy flux near the target site, while insufficient to ablate the tissue, is sufficient to cause trauma.

Application of RF electric currents emanating from electrode tips offers the advantage of greater localization of the energy deposition since the electrode tip is nearly a point source. However, these devices require consideration and accurate monitoring of the time rate of energy transfer to the tissue. Since the electric energy flux is localized, the electrical dissipation and storage characteristics of the tissue carrying the current may vary with time as a result of the current-induced heating. Thus, the power absorbed by the tissue could vary over the time of treatment due to changing values of the tissue's electrical properties.

The localization of energy flux in an RF electro-surgical device may require a number of electrodes to be included in the surgical probe to provide adequate area coverage. This may result in the electric power being delivered across several current paths. With multiple electrodes in a surgical probe, each probe electrode may or may not be at the same electric potential at each instant due to amplitude, frequency, or phase variations in their RF oscillations. If each probe electrode is at the same potential, then a current will flow between the probe electrode and the ground pad. This mode of operation is termed monopolar. If, however, each probe electrode is not an identical potential, current will flow between the probe electrodes. This mode of operation is termed multipolar. If there are potential differences between the probe electrodes and there is a ground pad, then there are currents between the probe electrodes as well as currents between the probe electrodes and the grounding pad. This model of operation is a combination of monopolar and multipolar modes. It is noteworthy that in the case of multipolar operation, the probe electrodes are electrically coupled by the currents flowing between them. The extent of the coupling is primarily determined by the difference in electric potential between the probe electrodes and the electrical properties of the tissue between the electrodes. This coupling can confuse monitoring of applied power and tissue response.

Power control is critical in an RF electro-surgical device since it is directly related to the intended medical effects. As described, the power absorbed by the tissue can vary over the time of treatment due to changing values of the tissue's electrical properties. This variation is due to a relation well-known to those skilled in the art in which the instantaneous power delivered to the tissue load is proportional to the square of the electrode voltage and inversely proportional to the tissue electrical impedance. Thus, to achieve equal power delivery, two surgical probe electrodes may have to be at different electric potentials (voltages) because of Joule heating effects on the tissue electrical impedance, or because of impedance gradients in the tissue. When the surgical probe electrodes are at different electric potentials, a current will flow between the electrodes. This electrode coupling is commonly referred to as cross-talk. Cross-talk confuses accurate power determination in most RF electro-surgical devices and thus there is a need for improved methods to control power delivery.

SUMMARY OF THE INVENTION

Methods and apparatus for power delivery and control in electro-surgery are fundamental to the intended medical benefits. During tissue heating, any electrode coupling confuses interpretation of power measurements by providing multiple current paths from electrodes. This coupling is commonly referred to as cross-talk or multi-pole behavior. It is an object of the present invention to provide a multi-channel radio frequency (RF) power delivery and control system for applying energy to multiple electrodes of an RF tissue heating device with independent control of the amplitude, frequency, inter-electrode phase and time duration of the energy applied to each electrode. This results in accurate, controlled heating of the target tissue.

In a first embodiment of the invention an apparatus for controlling electrical cross-talk in an electro-surgical instrument is disclosed. The apparatus includes: a driver, a first electrode, a second electrode, a ground for delivery of power to a surgical site, a power measurement circuit and a waveform generator. The power measurement circuit computes differences between a target power and an actual power delivered to the first electrode and the second electrode to establish an amount by which to increase and to decrease the power emanating from the first electrode and the second electrode. The waveform generator modulates a driver signal generated by the driver to increase and to decrease an integer number of whole wavelengths of the driver signal to produce a first oscillating signal measured at the first electrode and a second oscillating signal measured at the second electrode.

In an alternate embodiment of the invention a method for power control in an electro-surgical instrument is disclosed. The electro-surgical instrument includes a driver, and at least one electrode and a ground for delivery of power in the form of a first oscillating signal to a surgical site. The method for power control comprises the acts of:

computing differences between a target power and an actual power delivered to the at least one electrode to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

In another embodiment of the invention a method for power control in an electro-surgical instrument is disclosed. The method comprises the acts of:

computing differences between a target power and an actual power delivered to the first electrode and the second electrode to establish an amount by which to increase and to decrease the power emanating from the first electrode and the second electrode; and modulating a driver signal generated by the driver to increase and to decrease an integer number of whole wavelengths of the driver signal to produce a first oscillating signal measured at the first electrode and a second oscillating signal measured at the second electrode, responsive to said computing act.

DETAILED DESCRIPTION

This invention utilizes a novel method to control power delivery and inter-electrode coupling in a multi-electrode RF electro-surgical device. While the amplitude, frequency, and phase of the electrode voltages are adjustable in the system, the power delivery and inter-electrode cross-talk is controlled by introducing null intervals into the electrode's RF voltage wave train by means of switching.

Figure 1A:
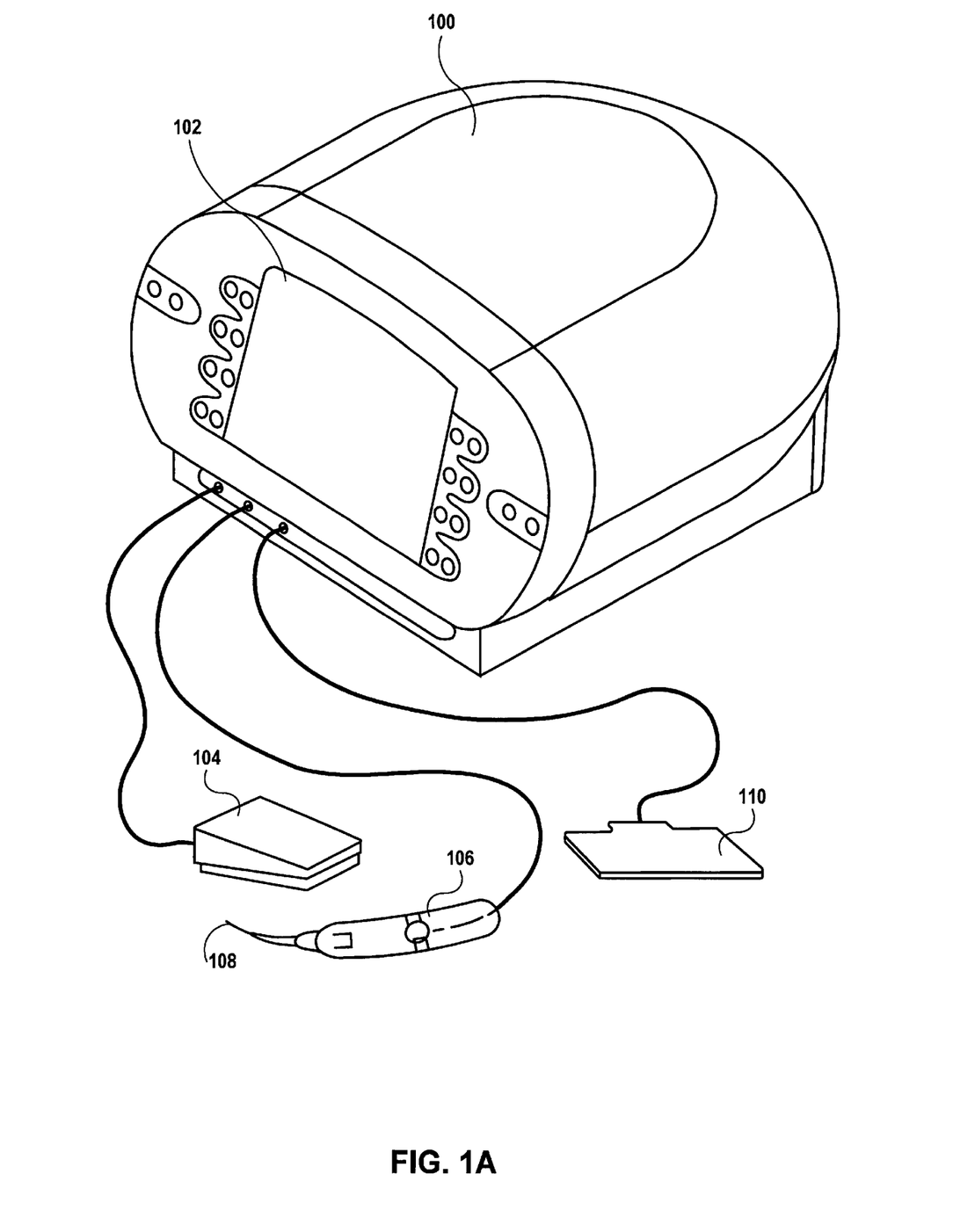
FIG. 1A shows an illustrative embodiment of a RF treatment system.

FIG. 1A shows the apparatus for a typical embodiment of the RF electro-surgical device. The system comprises an RF power supply 100 with a user input and display panel 102, a foot switch 104, a surgical handset 106 with a surgical probe 108 and an electrical grounding pad 110.

The RF power supply 100 converts the low frequency electrical energy supplied by a wall connection (not shown) into the high frequency or RF energy necessary for surgery. The user input and display panel 102 displays relevant parameters and provides buttons and switches for user input to the control systems. The foot switch 104 connected to the power supply provides means for switching off the unit should there be an emergency. The surgical handset 106 is also connected to the power supply and is the means for delivering the RF energy to the surgical probe 108. The probe has one or more electrodes. The electrical grounding pad 110 is also connected to the power supply. Other embodiments have no grounding pad.

Figure 1B:
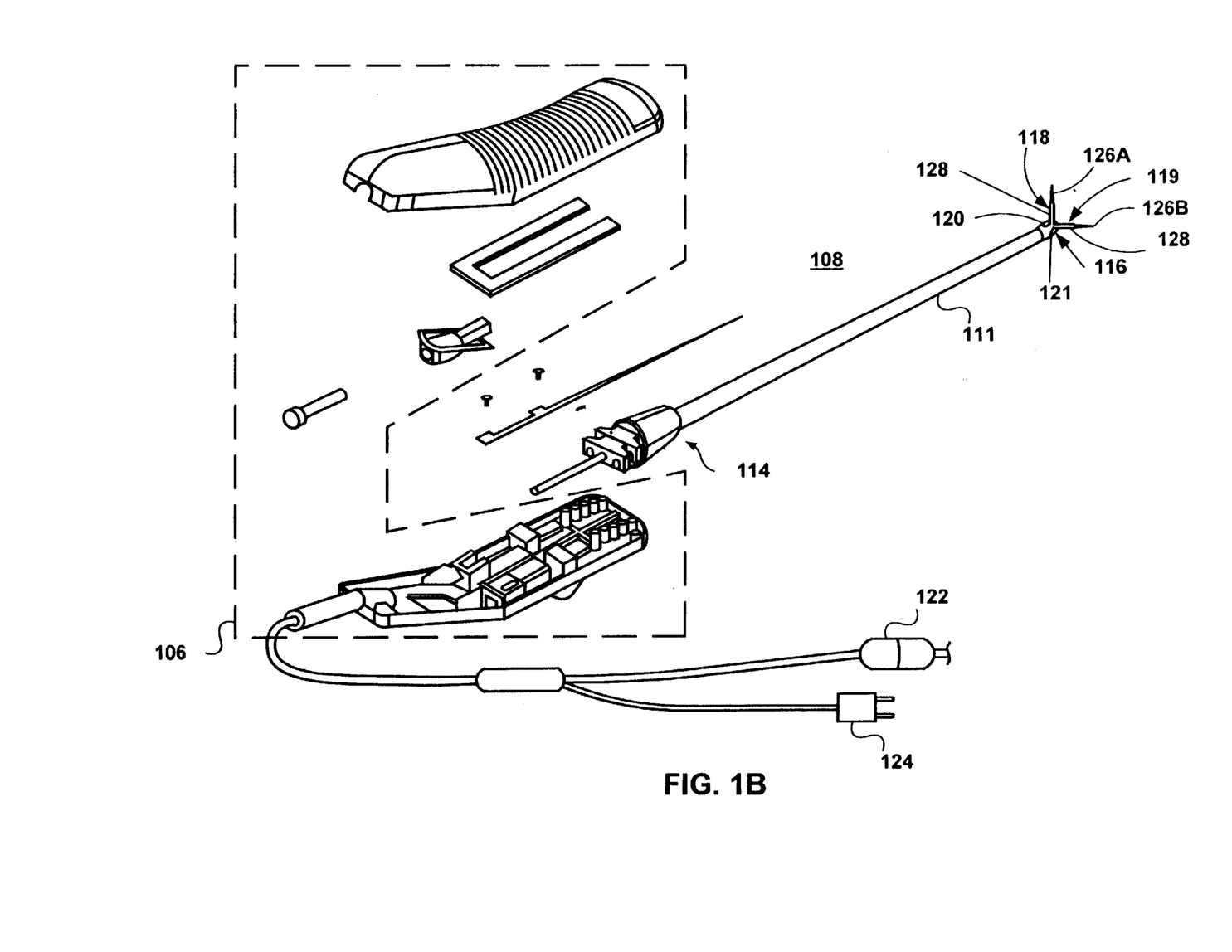
FIG. 1B shows an exploded perspective view of the surgical handset.

FIG. 1B is an exploded perspective view of the surgical handset 106 and surgical probe 108. As shown, the surgical probe 108 includes a flexible catheter 111 which is attached to a control unit 106 by a connector 114. The flexible catheter 111 includes a distal tip 116 having two stylets 118, 119, which extend outward from stylet ports 120, 121. Each stylet has a probe electrode 126A–B. The surgical handset 106 includes an RF power connector 122 and a thermocouple connector 124.

The flexible catheter 111 preferably has a stiffness gradient for easier insertion through a natural body opening into a body duct. For example, the flexible catheter 111 can be relatively stiff near the surgical handset 106 and more flexible near the distal tip 116. The flexible catheter 111 can be constructed of an inner slotted stainless steel tube with an outer flexible sleeve, such as the catheter described in detail in copending application Ser. No. 08/126,431 filed Sep. 24, 1993, now U.S. Pat. No. 5,322,064, the entire contents of which are incorporated herein by reference. The catheter may also be constructed of a coiled or braided wire having a bonded outer sleeve.

Figure 1C:
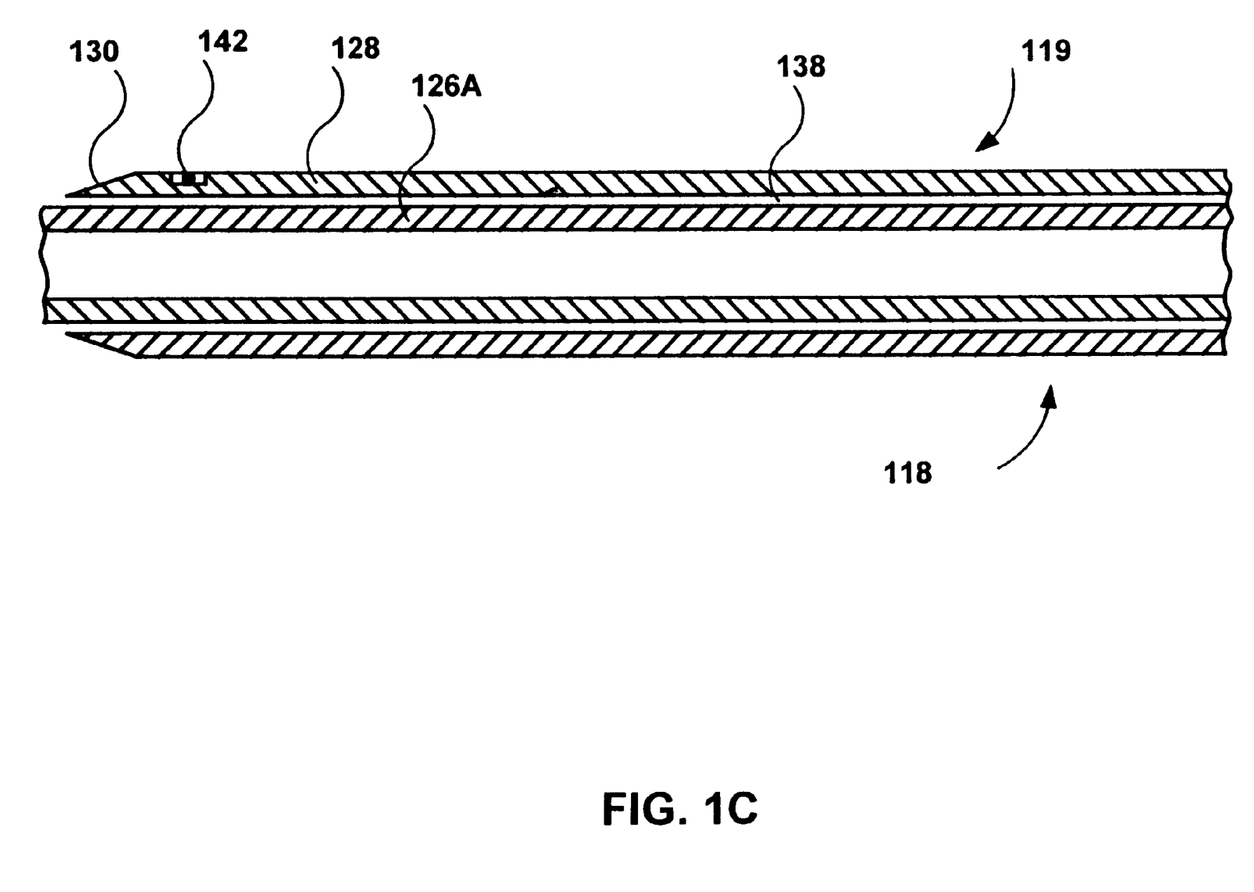
FIG. 1C shows a cross-sectional view of a stylet of the RF heating device.

FIG. 1C is a cross-sectional view of a stylet such as 118 or 119. Each stylet includes a probe electrode 126A–B enclosed within a retractable insulating sleeve 128. The stylets are described in detail in the copending application Ser. No. 08/012,370 filed Feb. 2, 1993, now U.S. Pat. No. 5,370,675. As shown in FIG. 1C, the insulating sleeve 128 has a tapered tip 130. The probe electrode 126 is disposed in the center portion 138 of the insulating sleeve 128 such that it can slide within the sleeve. A thermocouple 142 is mounted near the tapered tip 130 of the insulating sleeve 128 for measuring the temperature of a target tissue as it is heated.

Figure 2:
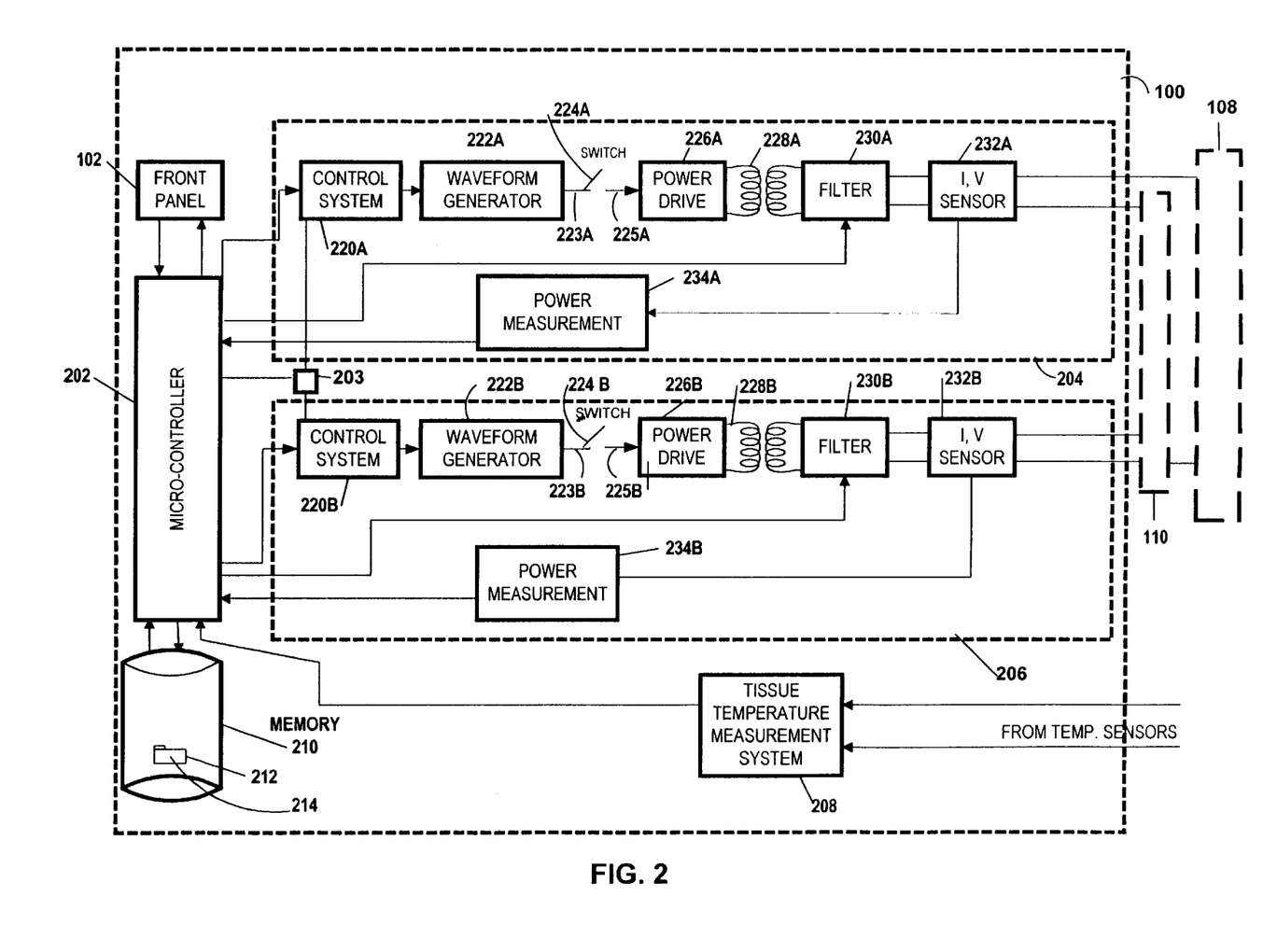
FIG. 2 shows a block diagram showing elements of the system architecture.

FIG. 2 shows a block diagram showing elements of the system hardware architecture of an exemplary embodiment. FIG. 2 shows a block diagram of the RF power supply 100, surgical probe 108 and grounding pad 110. Within the power supply, the user input and display panel 102, micro-controller 202, first and second electrode channels 204 and 206, tissue temperature measurement system 208, memory unit 210, memory files 212, control parameter schedule 214, and RF oscillator 203 are indicated. Electrode channels 204 and 206 are identical, each comprising a control system 220A–B, waveform generator 222A–B, an isolation switch 224A–B, a power drive 226A–B, a transformer 228A–B, a filter 230A–B, current and voltage sensors 232A–B, and power measurement system 234A–B.

In FIG. 2, the user input and display panel 102 is connected to the micro-controller 202 which is connected to the memory unit 210 including memory files 212, including a control parameter schedule 214. Exemplary control parameters are power and tissue temperature at the surgical site. Other control parameters are apparent to persons skilled in the art. The micro-controller is connected with the identical electrode channels 204 and 206 and also to the tissue temperature measurement system 208 and the RF oscillator 203. Within each electrode channel, the control systems 220A–B are connected to the micro-controller as well as to the RF oscillator and the tissue temperature measurement system. The control system also connects to the waveform generators 222A–B. The waveform generators are connected to the power drive 226A–B through the isolation switch 224A–B. It is obvious to those skilled in the art that the isolation switch 224A–B may be located elsewhere than shown in FIG. 2. It is equally obvious that the function of the isolation switch can be performed by other elements in FIG. 2 such as the microcontroller, control system, waveform generator, power drive, filter or electrode. The RF signals from the transformer 228A–B feed into filter 230A–B. The current and voltage sensors 232A–B connect to the filter, grounding pad 110, surgical probe 108 and the power measurement systems 234A–B.

The micro-controller 202 implements control programs and logic contained in memory files 212, providing the principal intelligence of the control system including the selection of values for time scales and power levels. In other embodiments, control is accomplished by analog hardware in control system 220A–B. In this alternate embodiment the micro-controller downloads new target values to the control system 220A–B. The control system 220A–B uses these new values as well as power measurements performed by the power measurement system 234A–B to adjust the drive level to the waveform generators 222A–B so as to minimize the error between target power and actual power delivered by the channels. To act as a means for control, the micro-controller is in two way communication with the user through user input and display panel 102 as well as receives input from the RF oscillator 203, and power and tissue temperature measurement systems 234A–B, 208A–B. Control variables are passed to control systems 220A–B and filters 230A–B to achieve the desired amplitude, frequency, and phase of the electrode potentials. The RF oscillator and waveform generator 222A–B generate RF oscillations, termed a driver signal. The driver signal, or a modulated driver signal incorporating on-off switching with the driver signal, drives the output of the power drive 226A–B. The modulation of the driver signal is determined by the micro-controller. It is obvious to persons skilled in the art that switch 224A–B may be located in a variety of positions other than shown in the embodiment of FIG. 2. Power is coupled through transformer 228A–B by the principle of induction, isolating the patient from direct current (DC). Further frequency filtering is accomplished by filter 230A–B. Current and voltage sensors 232A–B provide required signals for the power measurement systems 234A–B to determine the actual, aka true power or nonreactive, power transferred to the tissue by the current passing between the surgical probe 108 to grounding pad 110.

Micro-controller 202 can differentially control the voltage waveforms of each electrode in the surgical probe 108. By altering the amplitude or frequency, as well as by introducing null intervals to the voltage applied to each electrode tip, the electric power transferred to the tissue in the face of changing tissue electrical impedance can be controlled over the time of the surgical procedure. In other embodiments, this is accomplished by analog hardware in control system 220A–B. In this alternate embodiment the micro-controller downloads new target values to the control system 220A–B. The control system 220A–B uses these new values as well as power measurements performed by the power measurement system 234A–B to adjust the power so as to minimize the error between target power and actual power delivered by the channels.

Figure 3A:
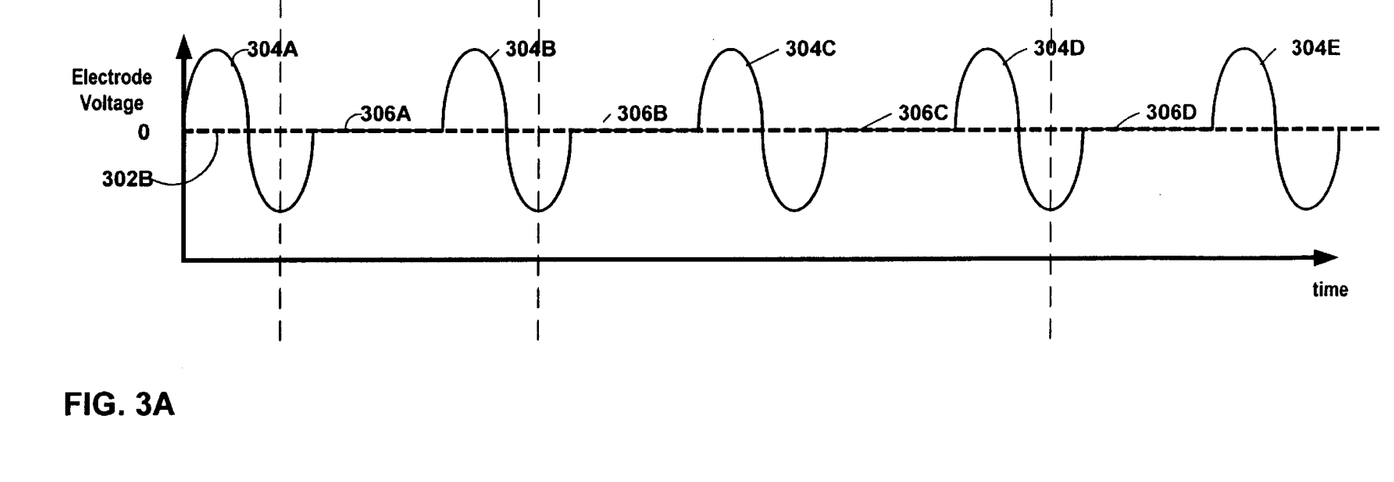
FIG. 3A shows electrode voltage versus time for an electrode at a lower than reference impedance, illustrating the use of null cycles for controlling multi-pole operation.
Figure 3B:
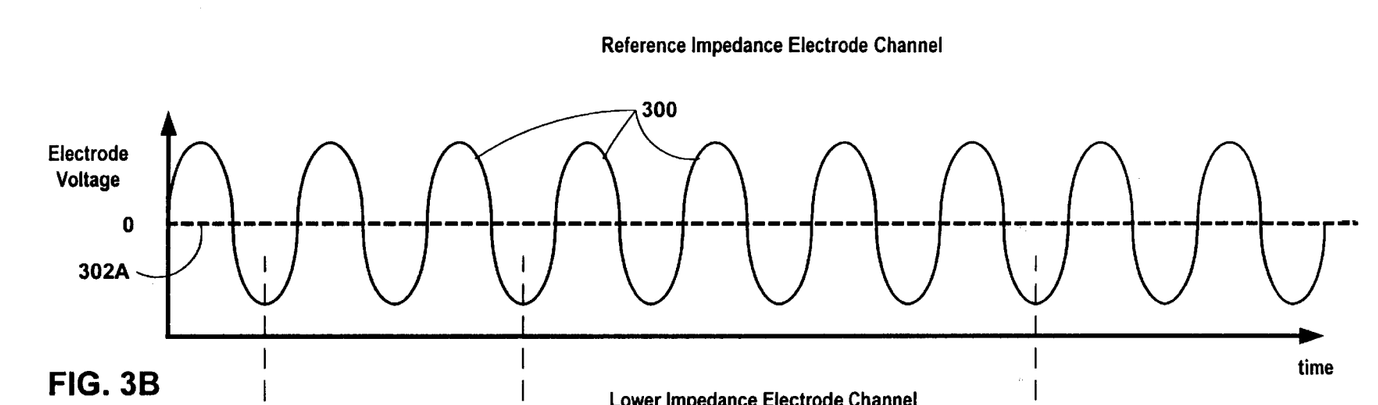
FIG. 3B shows electrode voltage versus time for an electrode at a reference impedance.

FIG. 3A and FIG. 3B show the electrode voltage (monopolar mode) versus time for two electrodes illustrating the novel use of null intervals to control power delivery and multi-pole operation. The electrode of FIG. 3B delivers power across tissue with a given reference electrical impedance. The electrode of FIG. 3A delivers power across tissue with a comparatively smaller impedance. RF voltage wavetrain 300, and voltage wavelets 304A–E oscillate about null crossing 302A–B. By removing wave cycles by means of switch 224A–B (see FIG. 2) at the lower impedance electrode, the electric power delivered to the tissues (equal to the electrode voltage squared divided by the impedance) at both sites can be matched over tissue heating time scales.

In the preferred embodiment, only full waves are nulled. Arbitrary nulling results in both high and low frequency Fourier signal components that affect the other medical electronics and the patient, respectively. Half-wave nulling could cause the patient to accumulate charge due to the current-voltage lag caused by tissue capacitance and inductance.

In another embodiment, a constant voltage source can be used. Since the voltage is constant in this embodiment, the use of a voltage sensor is not required During a null period, an inter-electrode current driven by their potential difference (bipolar mode) is prevented in the preferred embodiment by connecting the nulled electrode to an extremely high impedance. If a strictly monopolar delivery is desired after the null period, the RF cycles are resumed in phase with those of the other electrode thereby avoiding any bipolar effects. In an alternate embodiment, the RF cycles may be resumed out of phase and the resulting electrode potential difference will drive an interelectrode current.

Figure 4:
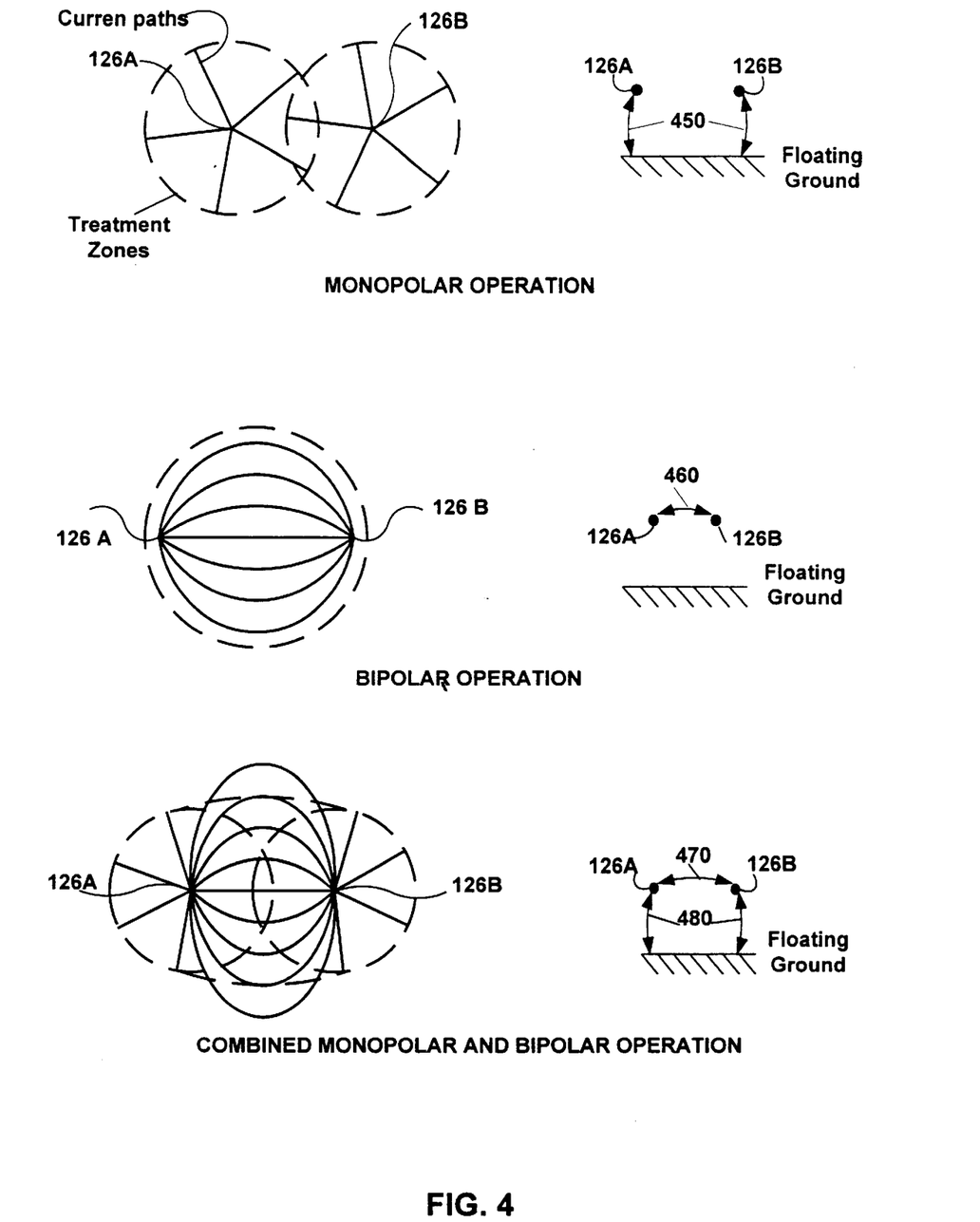
FIG. 4 illustrates the monopolar, multipolar and combined monopolar/multipolar modes of operation.

FIG. 4 illustrates the monopolar, multipolar and combined monopolar/multipolar modes of operation. Two probe electrodes 126A–B are shown. In monopolar operation, current 450 flows due differences in electric potential between the electrodes 126A–B and the floating ground provided by either the grounding pad or other electrode (not shown). There is no inter-electrode current. It is obvious to persons skilled in the art that elements other than the grounding pad can be substituted equivalently, for example an electrode connected to a floating ground. In the bipolar mode of operation, the ground pad is removed from the circuit either physically or effectively by connecting it to an extremely large impedance. In bipolar operation, current 460 flows between the probe electrodes 126A–B due to the differences in electric potential. There is no current flow to the ground pad. Multipolar operation is an extension of bipolar operation with more than two probe electrodes. Combined monopolar and bipolar operation occurs when potential differences drive currents both to the floating ground 480 and between the electrodes 470. Note that the extent of the treatment zone is affected by the mode of operation.

A significant advantage of the present invention is the availability of a combined monopolar and bipolar mode of operation in addition to a purely monopolar mode. In the monopolar mode, the same RF voltage signal is applied to each probe electrode 126A–B (see FIG. 1B) and current flows from the electrodes to an indifferent ground pad electrode placed in contact with the patient. Since the control system maintains the two probe electrodes 126A–B at the same potential, no current flows between them. Current only flows between each electrode and the electrical ground pad. However, by changing the amplitude, frequency or phase of one of the RF signals, a potential difference is created across the probe electrodes 126A–B and current flows between them. This provides combined monopolar and bipolar operation. Combined monopolar and bipolar operation allows a larger tissue volume to be heated as shown in FIG. 4.

Figure 5A:
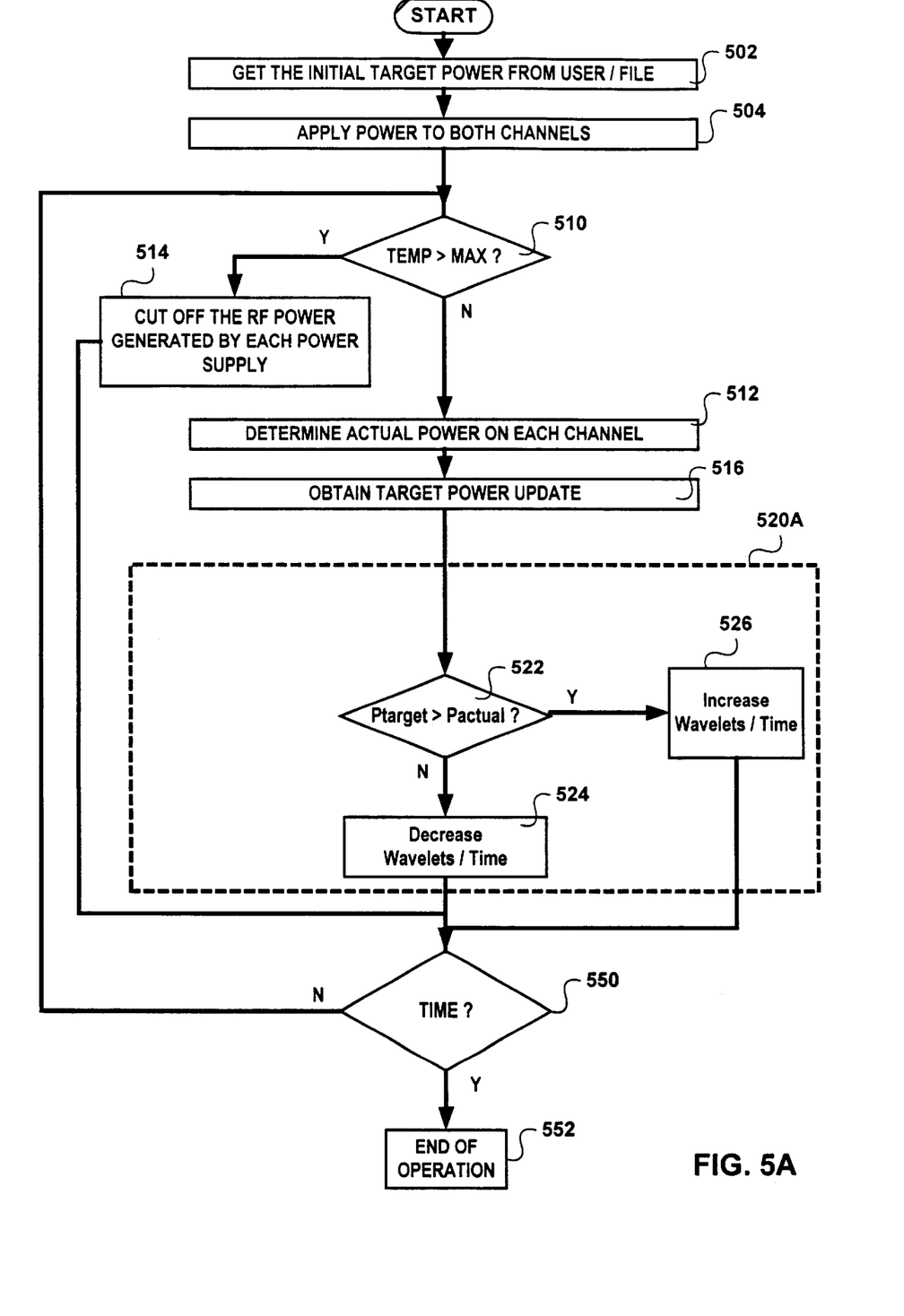
FIGS. 5A–B show process flow diagrams for alternate embodiments of the method for multi-electrode power delivery of the present invention.
Figure 5B:
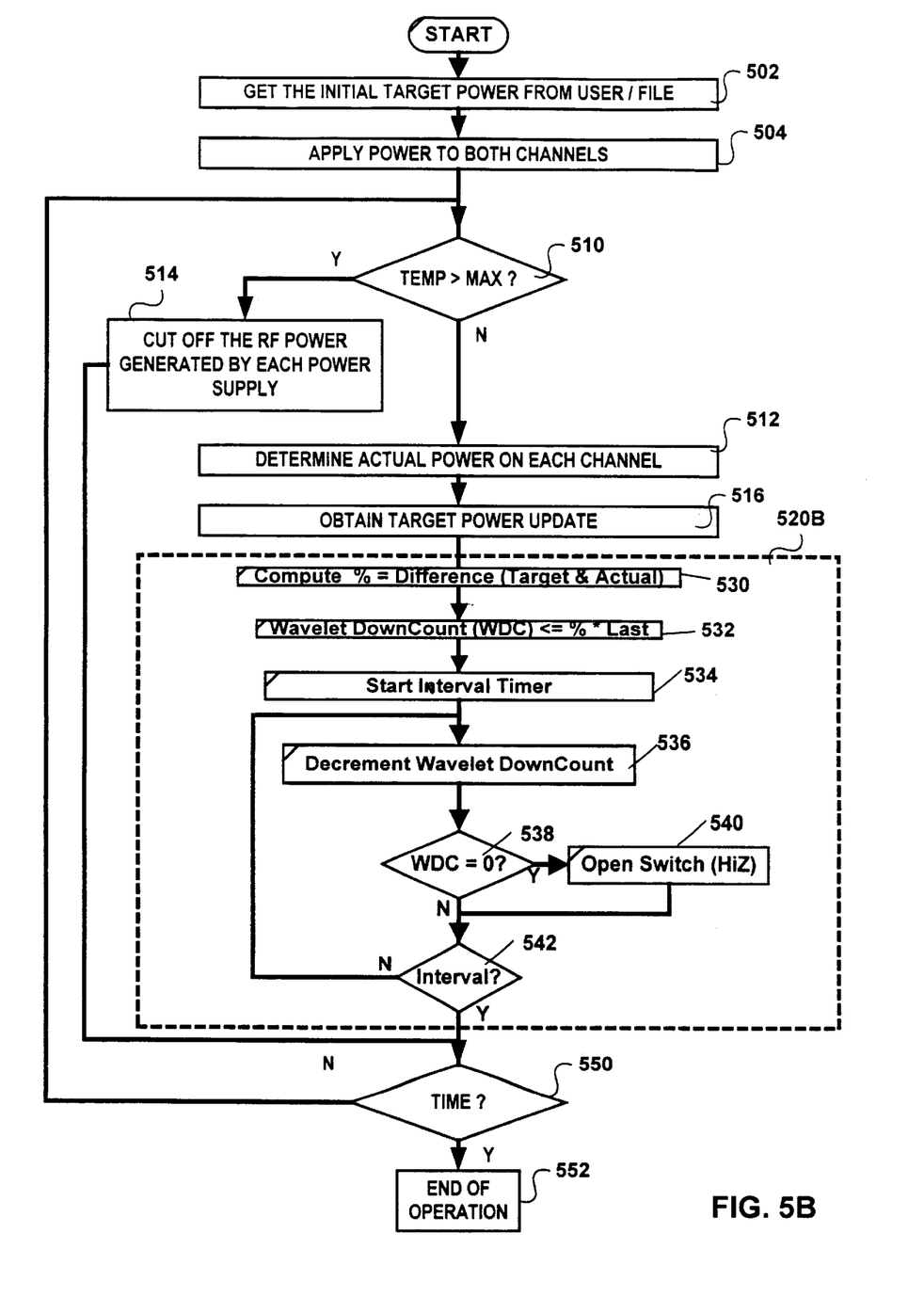

FIG. 5A and FIG. 5B show flowcharts for the RF wave cycles adjustment process for a two electrode embodiment. The processes shown in FIGS. 5A–B is implemented by the micro controller 202 (see FIG. 2). In FIG. 5A, the process begins in block 502 where an initial value for the target power is obtained from either the user input and display panel 102 or memory unit 210. Control then passes to block 504 where electric power is applied to the tissue through the electrodes. Control then passes to decision block 510 where a determination is made whether the tissue temperature exceeds a predetermined maximum. If the maximum tissue temperature is exceeded, RF power is cut off in process block 514. If the tissue temperature is not exceeded, control passes to process block 512 where the power delivered to the tissue is determined by power measurement system 234A–B (see FIG. 2). Control then passes to process block 516 where an updated target value for the power corresponding to the surgical time is obtained from memory unit 210. Control then passes to control sequence 520A where the null periods are determined, thereby altering the applied power. In the preferred embodiment, the null intervals are applied at every other wave cycle when nulling is required. The thermal lag of the tissue response integrates the effect of this quantized (full on-half nulled-full off) range.

In control sequence 520, a determination is made at decision block 522 whether the target value for the power exceeds the power actually delivered to the surgical site, as determined by the power measurement system 234A–B (see FIG. 2). In the case that the actual power delivered to the surgical site is less than the target value, null periods are removed to increase the applied power. In the case that the actual power delivered to the surgical site is greater than the target value, null intervals are added to decrease the applied power in process block 524. If necessary, null intervals are removed in process block 526. Control then passes to decision block 550 where a determination is made whether the surgical time is expired. If the surgery continues, control passes to decision block 510 where the measured tissue temperature is again compared to a predetermined value. If the surgery is finished, process block 552 stops the operation.

FIG. 5B shows detail of control sequence 520B where the null intervals are implemented. The process flow is as described in FIG. 5A up to block 516. In process block 530 micro controller 202 (see FIG.2) computes the difference between the target value of power and that actually delivered relative to the actually delivered power. Control then passes to process block 532 where the relative error calculated in block 530 is used to correct the number of voltage wavelets 304A–E per unit time that are passed to the tissue. This integer value is stored in a wavelet down counter in micro controller 202 (see FIG. 2). Control then passes to block 534 that begins a control time interval over which RF wavelets are counted. The preferred interval is an integer multiple of the inverse RF frequency and is approximately one second in duration. Control then passes to block 536 where the wavelet down counter decrements after each time period corresponding to the inverse RF frequency. Control then passes to decision block 538 where a determination is made whether the down counter has reached zero, indicating a null interval is to commence. If a null interval 306A–D (see FIG. 3A) is to commence, the electrode to be nulled has voltage removed and is switched to a extremely large impedance circuit element to prevent any current flow in process block 540. If the down counter indicates by a nonzero value that a null interval is not desired, the electrode remains active in an active interval. Control then passes to decision block 542 where a determination is made whether the control time interval is finished. Control then passes to decision block 550 where a determination is made whether the surgical time is expired. If the surgery continues, control passes to decision block 510 where the measured tissue temperature is again compared to a predetermined value. If the surgury is finished, process block 552 stops the operation.

From the foregoing, it will be appreciated that the present invention represents a significant advance in the field of RF electro-surgical devices. Although several preferred embodiments of the invention have been shown and described, it will be apparent that other adaptations and modifications can be made without departing from the spirit and scope of invention. Accordingly, the invention is not to be limited, except as by the following claims.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art.

What is claimed is:

1. A method for power control in an electro-surgical instrument including a driver, and at least one electrode and a ground for delivery of power in the form of a first oscillating signal to a surgical site, and the method for power control comprising the acts of:

computing differences between a target power and an actual power delivered to the at least one electrode to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

2. The method of claim 1, wherein said modulating act further comprises the act of:

switchable decoupling the at least one electrode from the driver signal to decrease by the integer number of the whole wavelengths the first oscillating signal.

3. The method of claim 1, wherein said modulating act further comprises the act of:

establishing a control interval corresponding to a first integer number of characteristic wavelengths of the driver signal;

implementing an active interval in the first oscillating signal in which the first oscillating signal corresponds with the driver signal;

implementing a null interval in the first oscillating signal by decoupling the driver signal from the electrode.

4. The method of claim 1, wherein the decoupling in said act of implementing a null interval results in said first oscillating signal exhibiting a null level.

5. A method for power control in an electro-surgical instrument including a driver, a first electrode and a second electrode and a ground for delivery of power to a surgical site, and the method for power control comprising the acts of:

computing differences between a target power and an actual power delivered to the first electrode and the second electrode to establish an amount by which to increase and to decrease the power emanating from the first electrode and the second electrode; and modulating a driver signal generated by the driver to increase and to decrease an integer number of whole wavelengths of the driver signal to produce a first oscillating signal measured at the first electrode and a second oscillating signal measured at the second electrode, responsive to said computing act.

6. The method of claim 5, wherein said modulating act further comprises the act of:

switchably decoupling the first electrode from the driver signal to decrease by the integer number of the whole wavelengths the first oscillating signal, to avoid an electrical crosstalk between the second electrode and the first electrode; and switchably decoupling the second electrode from the driver signal to decrease by the integer number of the whole wavelengths the second oscillating signal to avoid an electrical crosstalk between the first electrode and the second electrode.

7. The method of claim 5, wherein said modulating act further comprises the act of:

establishing a control interval corresponding to a first integer number of characteristic wavelengths of the driver signal;

implementing active intervals in the first oscillating signal and the second oscillating signal in which the first oscillating signal and the second oscillating signal correspond with the driver signal; and implementing null intervals in the first oscillating signal and the second oscillating signal by decoupling the driver signal from the electrode.

8. The method of claim 5, wherein the decoupling in said act of implementing null intervals results in the first oscillating signal and the second oscillating signal exhibiting a null level.

9. The method of claim 5, wherein the decoupling in said act of implementing null intervals reduces an electrical crosstalk between the first electrode and the second electrode.

10. The method of claim 5, wherein the first oscillating signal and the second oscillating signal are phase synchronous.

11. An apparatus for controlling electrical cross-talk in an electro-surgical instrument including a driver, a first electrode and a second electrode and a ground for delivery of power to a surgical site, and the apparatus for controlling cross-talk comprising:

a power measurement circuit for computing differences between a target power and an actual power delivered to the first electrode and the second electrode to establish an amount by which to increase and to decrease the power emanating from the first electrode and the second electrode; and a waveform generator coupled to a power drive and an isolation switchs the waveform generator modulating a driver signal generated by the power drive to increase and to decrease an integer number of whole wavelengths of the driver signal to produce a first oscillating signal measured at the first electrode and a second oscillating signal measured at the second electrode.

12. The apparatus of claim 11, wherein the isolation switch decouples the first electrode from the driver signal to decrease by the integer number of the whole wavelengths the first oscillating signal, to avoid an electrical crosstalk between the second electrode and the first electrode;

and for switchably decoupling the second electrode from the driver signal to decrease by the integer number of the whole wavelengths the second oscillating signal to avoid an electrical crosstalk between the first electrode and the second electrode.

13. The apparatus of claim 11, further comprising:
a timer for establishing a control interval corresponding to a first integer number of characteristic wavelengths of the driver signal;
a logic unit for implementing active intervals in the first oscillating signal and the second oscillating signal in which the first oscillating signal and the second oscillating signal correspond with the driver signal; and
implementing null intervals in the first oscillating signal and the second oscillating signal by decoupling the driver signal from the electrode.

14. The apparatus of claim 11, wherein the decoupling results in the first oscillating signal and the second oscillating signal exhibiting a null level.

15. The apparatus of claim 11, wherein the decoupling reduces an electrical crosstalk between the first electrode and the second electrode.

16. The apparatus of claim 11, wherein the first oscillating signal and the second oscillating signal are phase synchronous.

* * * * *